United States Patent [19]
Akamatsu et al.

[11] Patent Number: 5,650,559
[45] Date of Patent: Jul. 22, 1997

[54] MALE STERILE PLANT SPECIES

[75] Inventors: Toyokazu Akamatsu, Kimitsu; Tsutomu Kagami; Hiromi Sato, both of Sodegaura; Toshio Shiga, Kisarazu, all of Japan

[73] Assignee: Sakata Seed Corporation, Yokohama, Japan

[21] Appl. No.: 220,373

[22] Filed: Mar. 30, 1994

[30] Foreign Application Priority Data

Jul. 14, 1993 [JP] Japan .................................. 5-174499

[51] Int. Cl.$^6$ .............................. A01H 5/00; C12N 5/14; C12N 15/05
[52] U.S. Cl. .................. 800/220; 800/200; 800/DIG. 15; 800/DIG. 16; 800/DIG. 17; 435/172.2; 47/58; 47/DIG. 1
[58] Field of Search ............................ 435/172.2, 240.47; 47/58, DIG. 1; 800/220, 200, DIG. 15, DIG. 16, DIG. 17

[56] References Cited
PUBLICATIONS

Exhibit A –Ikushugaku Zasshi (Jpn. J. Breeding), vol. 43 (Extra No. 1), p. 96, 1993.
Exhibit B –Ikushugaku Zasshi (Jpn. J. Breeding), vol. 38 (Extra No. 1), pp. 14–15.
Exhibit C –Ikushugaku Zasshi (Jpn. J. Breeding), vol. 41 (Extra No. 2), p. 520.
Exhibit D –Ikushugaku Zasshi (Jpn. J. Breeding), vol. 40 (Extra No. 2), p. 8, 1990.
Akamatsu, et al. "Lecture Summary of the Japanese Society of Breeding Science", vol. 43, Apr. 1, 1993.
Yarrow et al. 1990. Plant Cell Rep. 9(4):185–188.
Menczel et al. 1987 Plant Cell Reports 6(2):98–101.
Jourdan et al. 1989. Theor. Appl. Genet. 78(3):445–455.

*Primary Examiner*—David T. Fox
*Attorney, Agent, or Firm*—Oblon, Spivak, McClelland, Maier & Neustadt, P.C.

[57] ABSTRACT

Male sterile plants derived from backcrossing plants having various hybridized and pure Ogura cytoplasms derived from a Japanese radish to mediate male sterility with plants having various hybridized and pure nuclei derived from the genus Brassica.

3 Claims, 7 Drawing Sheets

MALE STERILE PLANT SPECIES

BACKGROUND OF THE INVENTION

This invention relates to novel methods for breeding and propagating a male sterile plant and three novel species of male sterile plant resulting from this method. In more detail, this invention relates to novel methods for breeding and propagating a male sterile plant based on a cell carrying a nucleus of a desired pure line as its nucleus and a cytoplasm mediating male sterility as its cytoplasm.

(1) Owing to rapid development of plant biotechnology of recent years, various means for improving plant varieties have been developed.

In those means for improving plant varieties, a male sterile stock occupies a very important position. For example, the seed collection from a $F_1$-hybrid of a vegetable belonging to the family Cruciferae is generally carried out by utilizing a "self-incompatible" inbreeding line in which fertilization is not done normally owing to the facts that pollen does not germinate, the pollen tube cannot elongate into the style, the growing speed of the pollen tube becomes lowered or discontinued, etc. in spite of pollination. pollination does not permit seed collection because said line, though it is monoclinous and the reproductive organs of both sexes mature simultaneously, is incompatible with itself. However, it has been known that there are some inbreeding lines from which it is difficult to obtain desired $F_1$-hybrids efficiently because they are weak in such "self-incompatibility" though they are excellent in their practical performance per se. If the production of a $F_1$-hybrid using a male sterile stock as a female parent is intended in such cases, pollen is not produced from said female parent and thus the efficient production of $F_1$- hybrid described above can be attained.

(2) With respect to said production of a male sterile stock, however, the following disadvantages are pointed out at present.

As one of the means for producing a male sterile plant, "the nucleus substitution technique" by which a nucleus of an already established male sterile plant is replaced by a nucleus of a desired plant can be enumerated.

According to this "nucleus substitution technique", a mitochondorial DNA known as a genetic resource of male sterility is preserved in a cytoplasm, whereby the male sterility per se is preserved.

However, with respect also to a chloroplast which is known to hold its own genes exerting a serious influence upon the expression of characters of a plant, the chloroplast of said male sterile stock as a parent stock is preserved simultaneously. Accordingly, in case a male sterile stock as a parent stock is not related to a stock offering a nucleus, there are cases where an unfavorable phenomenon for producing a plant is provoked by the interaction between said chloroplast and said cell nucleus.

For example, in case that a "nucleus-substituted type (Ogura) *Brassica campestris*" is produced by using the Ogura cytoplasm of a Japanese radish [Ogura, H; *Mem. Pac. Agri.*, Kagoshima Univ., vol. 6, pp. 39–78 (1968)] as a cytoplasm providing male sterility and a nucleus of a plant belonging to *Brassica campestris* represented by a Chinese cabbage as a nucleus, said plant suffered from chlorosis at low temperatures. In addition, the growth of a nectary is not recognized in said plant, so that it becomes difficult to attract an insect such as a honey bee or the like having a role of transporting pollen. Accordingly, it seems difficult to say that said plant is a favorable stock to be developed.

(3) Then, between the above Ogura radish cell and a plant belonging to *Brassica napus* (rapeseed), use as a male sterile stock of a somatic hybrid which is produced by fusing protoplasts of said plants has been studied. [Pelletier et al, *Mol. Gen. Genet.*, vol. 191, pp. 244–250 (1983)].

In such a somatic hybrid, the male sterility held by the Ogura radish cell is preserved, while a chloroplast derived from the Ogura radish cell simultaneously falls off and only a chloroplast of a plant belonging to the above genus Brassica is preserved. As a result of these effects of somatic hybridization, said somatic hybrid has several advantages in that the above chlorosis and unsatisfactory growth of a nectary become unrecognized.

However, there is a limit to the kind of plant belonging to the genus Brassica suitable for the above protoplast fusion from the technical viewpoint. Therefore, it is difficult at the present to freely produce a male sterile somatic hybrid, which a breeder intends, directly by the above protoplast fusion techniques.

SUMMARY OF THE INVENTION

Accordingly, the problem to be solved by the present invention lies in providing a novel method for breeding a plant which uses a male sterile stock having the above excellent characters and enables free development of such a somatic hybrid having male sterility as a breeder intends.

The present inventors intensively made a wider and deeper study in order to solve the above problem. As a result of it, they found that it was possible to produce a plant preserving said desired characters belonging to the genus Brassica and at once preserving male sterility useful for the production of a $F_1$-hybrid by back crossing the above somatic hybrid with a desired plant belonging to the genus Brassica.

That is, the gist of the present invention lies in the following matters.

(1) A method for breeding a male sterile plant, comprising back crossing a plant having male sterility obtained by protoplast fusion techniques based on a somatic hybrid plant cell which carries a cytoplasm mediating male sterility as well as a nucleus of a plant belonging to *Brassica oleracea* or a nucleus of a hybrid plant between a plant belonging to *Brassica oleracea* and a plant belonging to *Brassica campestris* with a plant belonging to *Brassica oleracea, Brassica campestris, Brassica napus* or *Brassica juncea* to breed a male sterile plant belonging to *Brassica oleracea, Brassica campestris, Brassica napus* or *Brassica juncea* which carries the above cytoplasm mediating male sterility as well as a highly pure nucleus of a plant belonging to said *Brassica oleracea, Brassica campestris, Brassica napus* or *Brassica juncea*.

(2) A method for breeding a male sterile plant according to the above (1), wherein the cytoplasm mediating male sterility is a cytoplasm obtained by recombining the Ogura cytoplasm.

(3) A method for propagating a male sterile plant, comprising back crossing a plant having male sterility obtained by protoplast fusion techniques based on a somatic hybrid plant cell which carries a cytoplasm mediating male sterility as well as a nucleus of a plant belonging to *Brassica oleracea* or a nucleus of a hybrid plant between a plant belonging to *Brassica oleracea* and a plant belonging to *Brassica campestris* with a plant belonging to *Brassica oleracea, Brassica campestris, Brassica napus* or *Brassica juncea* to breed a male sterile plant belonging to *Brassica oleracea, Brassica campestris, Brassica napus* or *Brassica*

*juncea* which carries the above cytoplasm mediating male sterility as well as a highly pure nucleus of a plant belonging to said *Brassica oleracea, Brassica campestris, Brassica napus* or *Brassica juncea*.

(4) A method for propagating a male sterile plant described in the above (3), wherein the cytoplasm mediating male sterility is a cytoplasm obtained by recombining the Ogura cytoplasm.

According to the present invention, a novel plant breeding method using a male sterile plant stock having excellent characters, which enables free production of such an somatic hybrid having male sterility as a breeder intends, is provided.

DETAILED DESCRIPTION OF THE INVENTION

Figure 1:
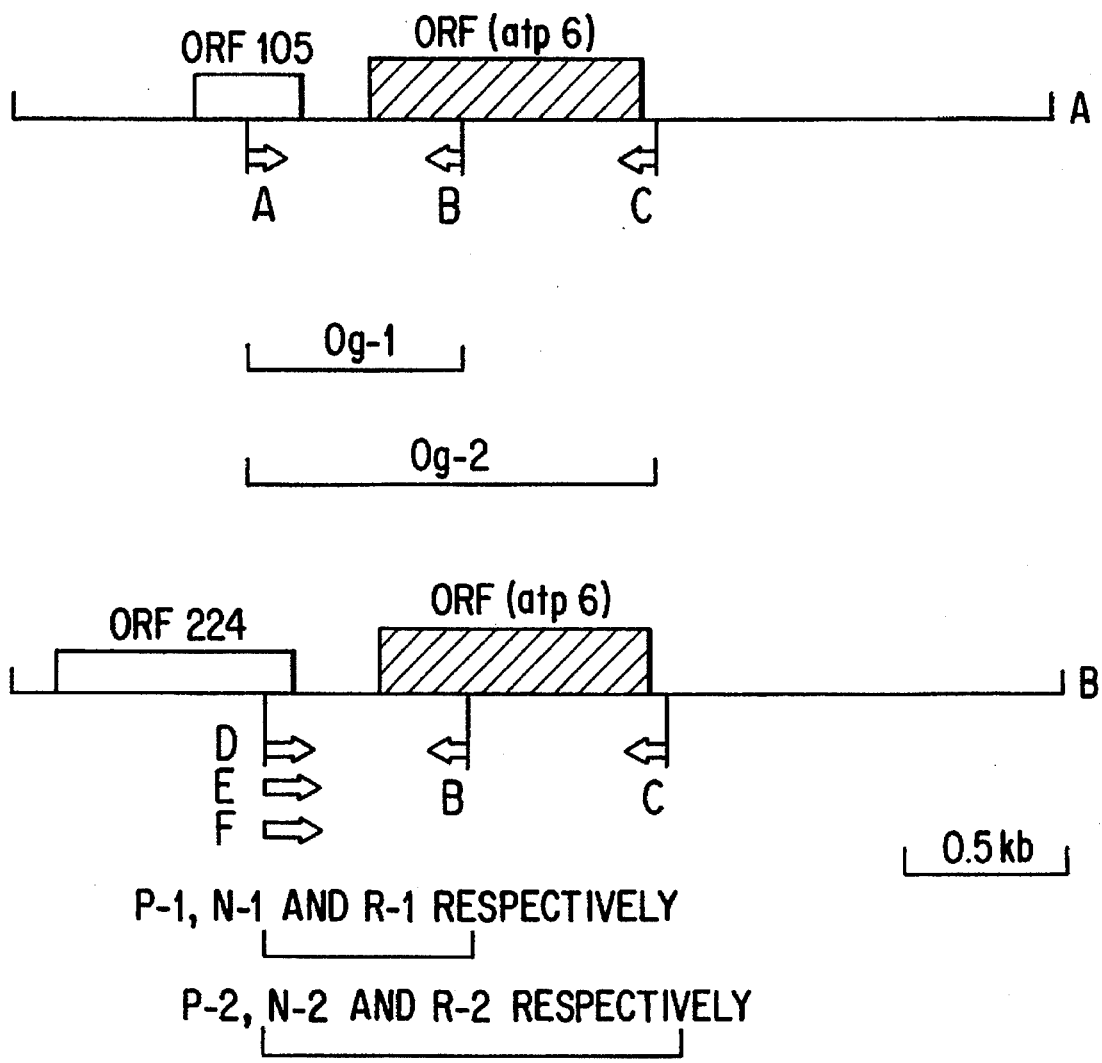
FIG. 1 is a view showing the origin of each PCR primer.

Hereinafter, the present invention is described in detail.

A. Production of a plant having male sterility based on somatic hybrid obtained by protoplast fusion techniques which carries a cytoplasm mediating male sterility as well as a nucleus of a plant belonging to *Brassica oleracea* or a nucleus of a hybrid plant obtained by a hybridization between a plant belonging to *Brassica oleracea* and a plant belonging to *Brassica campestris*

As examples of "a plant belonging to *Brassica oleracea*" from which a somatic hybrid cell can be prepared by making full use of protoplast fusion techniques here, a cabbage, a broccoli, a cauliflower, an ornamental kale, Brussels sprouts, a kohlrabi, a collard, a kairan (the albograbra group of *Brassica oleracea* L.), a kale, etc. can be enumerated, among which "Kinkei 201", a F1-hybrid variety and its parent line "F" (both of which were produced by SAKATA SEED CORPORATION) of a cabbage can be enumerated as particularly favorable plants because cells of said plants are easily isolated into protoplasts which can be fused with other protoplasts.

As examples of "a somatic hybrid plant between plants belonging to the genus Brassica" from which somatic hybrid cell can be prepared by making full use of protoplast fusion techniques, a hakuran (artificial synthesized *Brassica napus*), which is known as an interspecific hybrid of a hybrid of a cabbage and a Chinese cabbage, and the like can be enumerated. It has been known that it is originally difficult to fully apply the protoplast fusion techniques to a Chinese cabbage belonging to "*Brassica campestris*" [Jourdan, P. & E. D. Earle; *J. Amer. Hort. Sci.*, vol. 114, pp. 343–349 (1989)]. Accordingly, it is preferable to utilize a hakuran as "a somatic hybrid plant between plants belonging to the genus Brassica" to which protoplast fusion techniques can be fully applied according to the present breeding method because it can be a bridge plant for producing a male sterile Chinese cabbage.

As examples of a cytoplasm carrying mitochondoria mediating male sterility, the Ogura cytoplasm known as said cytoplasm derived from a Japanese radish, the SHIGA-THOMPSON cytoplasm and POLIMA cytoplasm known as said cytoplasm derived from a rapeseed, the ANANO cytoplasm known as said cytoplasm derived from a leaf mustard, the MURALIS cytoplasm known as said cytoplasm derived from *Diplotasis muralis*, etc. can be enumerated. Among these male sterility-mediating cells, the Ogura cytoplasm can be cited as particularly favorable one because a so-called restoring gene, which restores the fertility of a plant, is rarely expressed even if said cytoplasm is transferred into a plant of the genus Brassica and thus the male sterility per se can be preserved stably.

As protoplast fusion techniques which are techniques for preparing a somatic hybrid cell between a plant cell belonging to the above genus Brassica and a cell having a cytoplasm mediating male sterility in the present invention, ordinary techniques which are now applied to plant cells can be adopted [Kao N. K. and M. R. Michayluk; *Planta*, vol. 115, pp. 355–367 (1974)].

Specifically, cell walls are removed from plant cells intended to be fused to isolate protoplasts and then said protoplasts are fused each other. As examples of fusing methods in this case, the traditional technique using polyethylene glycol as a fusogen; the electrofusion technique comprising making a protoplasts to form "a pearl chain" electrically and applying direct current to this; etc. can be enumerated. Taking the fusion efficiency into consideration, however, the latter electrofusion technique can be cited as a favorable fusion technique.

After carrying out protoplast fusion, said fused protoplast can be further induced into a desired plant by culturing the same according to an ordinary known method. For example, the fused protoplast is cultured into a callus-breeding medium, the Yamashita & Shimamoto's medium [*Jpn. J. Breeding;* vol. 34, Supplement volume No. 2, p. 30–3 (1984)] to produce small calluses, then said small calluses are placed on regeneration media prepared by adding plant hormones such as cyto-kinin and the like to various basal media to breed the small calluses, and the desired plants can be induced.

Incidentally, which of the cells fused mitochondorial DNAs and chloroplast DNAs of the hybrid cell are derived from can be confirmed by extracting said DNAs and analyzing restriction enzyme patterns thereof, by the RFLP method using the known probe, or like method.

B. Back crossing of a somatic hybrid plant having male sterility obtained as aforementioned with a desired plant belonging to *Brassica oleracea, Brassica campestris, Brassica napus* or *Brassica juncea* to breed a male sterile plant belonging to *Brassica oleracea, Brassica campestris, Brassica napus* or *Brassica juncea* which carries the above cytoplasm mediating male sterility as well as a highly pure nucleus of a plant belonging to said *Brassica oleracea, Brassica campestris, Brassica napus* or *Brassica juncea.*

Said back crossing is carried out by directly back crossing a somatic hybrid plant having male sterility obtained as aforementioned with a plant belonging to *Brassica oleracea, Brassica campestris, Brassica napus* or *Brassica juncea* which is intended to be produced.

To mention about the frequency of such back crossing, the somatic hybrid plant gets closer to the pure line of a plant belonging to the genus Brassica as a result of the back crossing as the back crossing is repeated more frequently. And, with respect to characteristics of the cytoplasm during this period, those of a mother plant are preserved with repeated back crossing. That is, the aforementioned male sterility is preserved as it is in offspring plants irrespective of the frequency of said back crossing. In specific procedure of the back crossing, the ovule culture is jointly adopted on the order of the first two times and thereafter ordinary back crossing is carried out. Although the frequency of said back crossing depends upon the degree of relationship between a somatic hybrid plant having male sterility and a plant belonging to said genus Brassica which is intended to be produced and how pure a male sterile plant is intended to be produced, it is generally 5 times at least, preferably about 7 times.

In addition, the ovule culture method [Nishi et al.; *Jpn. J. Breed.,* vol. 8, pp. 215–222 (1959)] can be adopted jointly in the above back crossing in order to acquire progenies efficiently. In case, particularly, of carrying out remote hybridization of a plant between plants which are congeneric but xenogenic, the above joint adoption is preferable.

Incidentally, there is no restriction to a plant belonging to *Brassica oleracea, Brassica campestris, Brassica napus* or *Brassica juncea* as an object of this back crossing as far as it is a plant belonging to said genus Brassica.

As specific examples of the plant belonging to *Brassica oleracea,* a cabbage, a broccoli, a cauliflower, an ornamental kale, Brussels sprouts, a kohlrabi, a collard, a kairan (the albograbra group of *Brassica oleracea* L.), a kale, etc. can be enumerated. As specific examples of the plant belonging to *Brassica campestris,* a Chinese cabbage, a turnip, a chingensai (*Brassica rapa* L. var. *chinenis*), a komatsuna (*Brassica rapa* L. var. *pervidis*), Nabana(*Brassica rapa* L. var. *amplexicaulis*), a Nozawana(*Brassica rapa* L. var. *rapa*), a selection progeny of (a Chugokusaishin X an artificially synthesized rape seed), etc. can be enumerated. As specific examples of the plant belonging to *Brassica napus,* a rape seed, an artificially synthesized rape seed as a hybridization progeny of (Autumn poem X a broccoli), etc. can be enumerated. And, as specific examples of the plant belonging *Brassica juncea,* a leaf mustard, a headed leaf mustard, an oil leaf mustard, a takana (*Brassica juncea* Czern et Coss var. *integlifolia* Kitamura), a zaasai (*Brassica juncea* var. *bulbifera* Mas.), etc. can be enumerated. Among these, a combination in a male sterile somatic hybrid plant as a parent plant is Cabbage-Radish-MS-2 and a plant as an object of back crossing is the one belonging to *Brassica oleracea,* a combination in which said male sterile somatic hybrid plant is Hakuran MS-1 and a plant as an object of back crossing is the one belonging to *Brassica napus,* a combination in which said male sterile somatic hybrid plant is Hakuran MS-2 and a plant as an object of back crossing is the one belonging to *Brassica oleracea,* and a combination in which said male sterile somatic hybrid plant is Hakuran MS-3 and a plant as an object of back crossing is the one belonging to *Brassica campestris,* are favorable because of the ease of back crossing.

EXAMPLES

Hereinafter, the present invention is describe more specifically, referring to examples. However, the technical scope of the present invention is in no way restrictively interpreted because of said examples.

[Example 1]

(A) Production of male sterile fusion plant of the genus Brassica

1) Isolation of protoplasts having cytoplasms mediating male sterility

A Japanese radish having male sterile cytoplasms (Ogura) or a nucleus-substituted Chinese cabbage having said cytoplasms (Ogura) were aseptically preserved and cultured in a culture bottle for about 1 month, followed by cutting of leaves of the cultured plants. The cut leaves were treated with an enzyme solution containing 0.1% Pectlyase Y-23, 2% Cellulase Onozuka R-10 and 0.5 M mannitol at 28° C. for 2 hours. Then, protoplasts were purified and prepared using said enzyme solution according to an ordinary method [Nagata, T. and Takebe, I.; *Planta,* vol. 99, p. 12 (1971)].

With respect to the above male sterile nucleus-substituted Chinese cabbage, protoplasts were UV-irradiated for 120–180 seconds using a UV lamp in a clean bench after purification and then subjected to the following protoplast fusion process.

With respect to a Japanese radish, protoplasts purified above were directly subjected to protoplast fusion.

2) Preparation of protoplasts of a plant of the genus Brassica into which male sterile characters are transferred A leaf was collected from an aseptic seedling of a cabbage ($F_1$ variety "Kinshi 201" or its parent line "F"), from which protoplasts were prepared according to the above protoplast preparation method. The protoplasts isolated and purified according to such a preparation method were treated by immersing into 7.5 mM acetamide for 15 minutes, centrifuged at 800 rpm for 3 minutes to harvest protoplasts and then washed with a W5 solution to prepare the desired protoplasts.

3) Protoplast fusion

The protoplasts of a Japanese radish having male sterile cytoplasms (Ogura) obtained in the above 1) and the iodo-acetamide-treated cabbage protoplasts obtained in the above 2) were respectively treated to have a concentration of 1×10⁶ cell/ml. After mixing 1 ml portions of respective protoplasts, 3ml of 33% polyethylene glycol (hereinafter abbreviated to PEG) was added thereto and mixed.

Thereafter, a 0.1 M calcium chloride solution was added to the above mixture, followed by fusion at room temperature. Subsequently, the supernatant was cast away, and the fused cells were washed with a CPW solution [Freason et al.; *Dev. Biol.*, vol. 33, pp. 130–137 (1973)] and subjected to culture.

In case of fusing the UV-irradiated protoplasts of the nucleus-substituted Chinese cabbage having male sterile cytoplasm (Ogura) obtained in the above 1) and the cabbage protoplasts obtained in the above 2), both protoplasts were respectively adjusted to have a concentration of 1×10⁶ cells/ml in the same manner as above, and the above protoplasts were mixed in equal quantities. The cell fusion was carried out electrically using a Model 301 manufactured by BTX, Inc., where 30 V/cm of alternating current was applied to the mixed cells for 30 seconds and followed by application of 1,400 V/cm of direct current thereto for 20 μsec.

4) Culture of the fused protoplast and regeneration of a plant

After the above fusion treatment using a PEG solution or by electric pulses, the fused protoplast was cultured on callus growing medium [a modified MS medium containing 0.3 M mannitol, 0.5 mg/l 2,4-dichlorophenoxyacetic acid (hereinafter abbreviated to 2,4-D), 0.35 mg/l naphthaleneacetic acid (hereinafter abbreviated to NAA) and 0.5 mg/l benzylaminopurine (hereinafter abbreviated to BAP), followed by addition of a medium having the same composition except for 0.2 M mannitol on the 10th day from the beginning of culture. After 10 more days, colonies were transplanted to a 100-ml flask in which a similarly composed mannitol free medium had been placed and then rotated to culture at 2 rpm. After 7 days from said rotation culture, calluses grown to 1–2 mm length were subcultured on regeneration media [MS media containing 1 mg/l benzyladenine (BA)] to promote the induction of adventitious buds. Thus obtained adventitious buds were transplanted to BAP-free MS media. After rooting, the plantlets were bred by acclimating to the outdoor environment according to an ordinary method. After flowering, the conditions of pollen production of the plantlets were visually evaluated to select male sterile individuals.

5) Selection of male sterile plant

With respect to the presence of male sterility, the plants flowered in the aforementioned 4) were examined one by one.

As a result of the protoplast fusion of a Japanese radish having male sterile cytoplasm (Ogura) with a cabbage, a male sterile plant carrying the mixed karyotype of a cabbage and a Japanese radish (hereinafter, referred to as Cabbage MS-1) and a male sterile plant carrying the karyotype of a cabbage alone (hereinafter, referred to as Cabbage MS-2), each of which had well-developed nectaries and did not exhibit the yellowing of leaf color (referred to as chlorosis) at low temperatures, were obtained.

Incidentally, seeds of the above Cabbage MS-2 has been deposited in the ATCC as "Cabbage Cybrid CMS-2" with the accession No. ATCC 75488.

As a result of the protoplast fusion of a nucleus-substituted Chinese cabbage having male sterile cytoplasms (Ogura) with a cabbage, hakuran type male sterile plants respectively carrying 32, 44 and 34 chromosomes which all have well-developed nectaries and do not exhibit the yellowing of leaf color at low temperatures were obtained. Hereinafter, these plants are referred to as Hakuran MS-1, Hakuran MS-2 and Hakuran MS-3 respectively.

Incidentally, seeds of the above Hakuran MS-3 has been deposited in the ATCC as "Hakuran Cybrid CMS-3" with the accession No. ATCC 75489.

(B) Analyses by the PCR technique and the RFLP technique

Using 4 kinds of novel male sterile lines, that is, a male sterile variety Cabbage MS-2 obtained by the protoplast fusion of a Japanese radish having male sterile cytoplasm (Ogura) with a cabbage and male sterile varieties Hakuran MS-1, Hakuran MS-2 and Hakuran MS-3 obtained by the protoplast fusion of a nucleus-substituted Chinese cabbage having male sterile cytoplasms (Ogura) and a cabbage; a Japanese radish having (Ogura) cytoplasms used as resource of the conventional male sterile cells; and a fertile cabbage used for cell fusion ($F_1$ variety, Kinshi 201) as testing varieties, the analyses of mitochondorial DNAs and chloroplast DNAs were carried out according to the following PCR technique and RFLP technique.

1) PCR technique

From leaves on the 40th to 50th day from seeding, chloroplast DNA (hereinafter, abbreviated to cpDNA) and mitochondorial DNA (hereinafter, abbreviated to mtDNA) were extracted according to the Kemble (1987) method and subjected to PCR analysis. PCR primers, which were intended so that specific sites of mtDNAs of a Japanese radish having male sterile cytoplasms (Ogura), an ordinary male fertile Japanese radish, a male sterile rapeseed having S-type cytoplasms which had been already reported (Thomposon, 1972; Shiga, T. and Baba, S., 1973) and a male sterile rapeseed having Polima-type cytoplasms [Fu, T. D.; *Cruciferae News Letter*, vol. 6, pp. 6–7 (1981)]might be amplified, were prepared.

That is, primers, each of which was so intended as to amplify the range starting from the promoter part on 300-bp upstream of the transcription initiation site of DNA encoding ATPase subunit 6 in the above mtDNA [Kadowaki, K. et al; *Mol. Gen. Gent.*, vol. 224, pp. 10–16 (1990)] (hereinafter abbreviated to atp 6) to the midway (−1) or the whole (−2) of the structural gene (hereinafter abbreviated to ORF), were synthesized. Base sequences of respective primers A–F are A (Sequence No. 1), B (Sequence No. 2), C (Sequence No. 3), D (Sequence No. 4), E (Sequence No. 5) and F (Sequence No. 4).

The combinations and the objects of amplification of these primers are as follows:

| | |
|---|---|
| A + B: Og-1 | A + C: Og-2 |
| D + B: P-1 | D + C: P-2 |
| E + B: N-1 | E + C: N-2 |
| F + B: R-1 | F + C: R-2 |

Incidentally, among the above primers, the relationship between Og and R (Ogura and a Japanese radish) was designed by citing "Christopher A. Makaroff, Ingrid J. Ape and Jeffery D. Palmer; *The Journal of Biological Chemistry*, vol. 264, pp. 11706–11713 (1989)".

In addition, the relationship between N and P (Napus and Polima) was designed by citing "Mahipal Singh and Gregory G. Brown, *The Plant Cell*, vol. 3, pp. 1349–1362 (1991)".

And, the amplification was carried out by using said primers as PCR primers and mtDNAs of the above various male sterile fused cells as templates and repeating a heat cycle of 94° C. (1 minutes), 55° C. (1 minutes) and 72° C. (2 minutes) 30 times. The obtained PCR amplification products were analyzed by agarose electrophoresis.

With respect to chloroplast (cp) DNAs, the analysis was carried out using probes prepared by digesting chloroplast DNAs of *Brassica napus* with a restriction enzyme EcoRI and then integrating to clone the digests in Blue Script plasmids.

The results of these analyses were given in Table 1.

TABLE 1

PCR analyses in cpDNAs and mtDNAs of various male sterile fused cells

| Male Sterile Plant | | Og-1 | Og-2 | N-1 | N-2 | R-1 | R-2 | P-1 |
|---|---|---|---|---|---|---|---|---|
| Hakuran MS-1 | cp: | ++++ | ++++ | +++ | +++ | – | – | – |
| | mt: | ++++ | ++++ | – | – | – | – | – |
| Hakuran MS-2 | cp: | – | – | ++++ | ++++ | +++ | ++ | – |
| | mt: | + | – | ++++ | ++++ | +++ | – | – |
| Hakuran MS-3 | cp: | ++++ | +++ | + | + | – | – | – |
| | mt: | ++++ | ++++ | – | – | – | – | – |
| Cabbage MS-2 | cp: | – | – | ++++ | ++++ | + | + | – |
| | mt: | + | – | ++++ | ++++ | +++ | ++ | – |
| Cabbage | cp: | + | – | ++++ | ++++ | ++ | – | – |
| | mt: | ++ | + | ++++ | ++++ | ++ | + | – |
| Ogura CMS | cp: | ++++ | + | – | – | – | – | – |
| | mt: | ++++ | ++++ | – | – | – | – | – |

In Table 1, + means the degree of the presence of PCR product, and it means that the quantity of PCR product obtained becomes larger as the number of + increases. On the other hand, – means that no PCR product was obtained. In addition, cp means the case where a chloroplast DNA was used as a template and mt means the case where a mitochondorial DNA was used as a template. And, the ranges of amplification by various PCRs were given in Table 1.

From these results, it became clear that, in the case of the Hakuran MS-1 cytoplasm, a new PCR product could be obtained when the range of amplification by PCR was fixed for N-1 and N-2 as for the cpDNA, as compared with the (Ogura) male sterile cytoplasm existing in nature.

In addition, the Hakuran MS-2 cytoplasm formed PCR products by N-1 and N-2 in both the cpDNA and the mtDNA, as compared with the (Ogura) male sterile cytoplasm existing in nature.

On the other hand, the Hakuran MS-3 cytoplasm formed PCR products by N-1 and N-2 as for the cpDNA alone, as compared with the (Ogura) male sterile cytoplasm existing in nature.

And, the Cabbage MS-2 cytoplasm, as well as the aforementioned MS-2, formed PCR products by N-1 and N-2 as for both the cpDNA and the mtDNA.

2) RFLP technique

From the mesophylls of the male sterile cabbages MS-1 and MS-2 obtained by the protoplast fusion and the male sterile hakurans MS-1, MS-2 and MS-3 obtained by the protoplast fusion, mtDNAs were extracted according to the Kemble (1978) method and then digested with restriction enzymes BamHI and Hind III. Said DNA fragments were electrophoresed on 1% agarose and then subjected to Southern hybridization according to the Genlus system (manufactured by Boehringer Mannheim Co.). As probes to be used, DNA fragments encoding ATPase subunit α in the mtDNA of a rice plant [Kadowaki, K. et al.; *Nucleic Acids Res.*, vol. 17, No. 5 (1990)] (hereinafter, abbreviated to atp A), the aforementioned atp 6 and cytochrome oxidase subunit I [Kadowaki, K. et al.; *Nucleic Acids Res.*, vol. 17, No. 18 (1989)] (hereinafter, abbreviated to cox-I) were used.

Figure 2A:
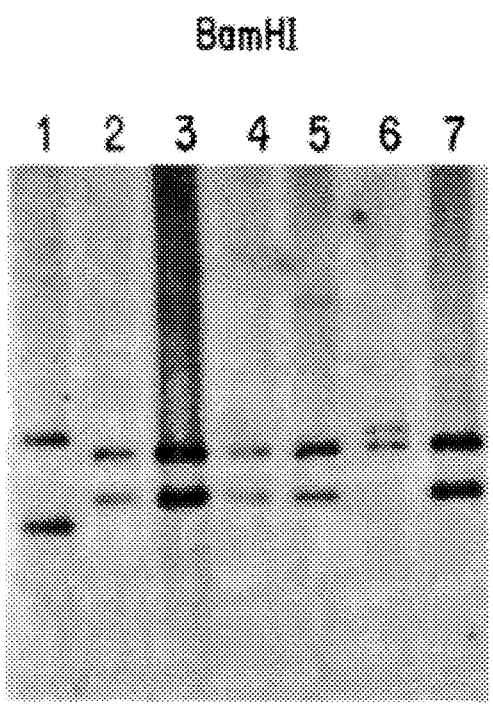
FIGS. 2A–2B are an electrophoretic pattern (1) showing the results of RFLP in mitochondorial DNAs of male sterile lines obtained by protoplast fusion (probe, atp A). Lane: 1. Cabbage; 2. Cabbage, Radish, MS-1; 3. Cabbage, Radish, MS-2; 4. Japenese radish (Ogura CMS), 5. Hakuran MS-1; 6. Hakuran MS-2; 7. Hakuran MS-3. Note: γ-Hind III digests used as markers, the size of which are 23.1 kbp, 9.4 kbp, 6.6 kbp and 4.4 kbp from the top.
Figure 2B:
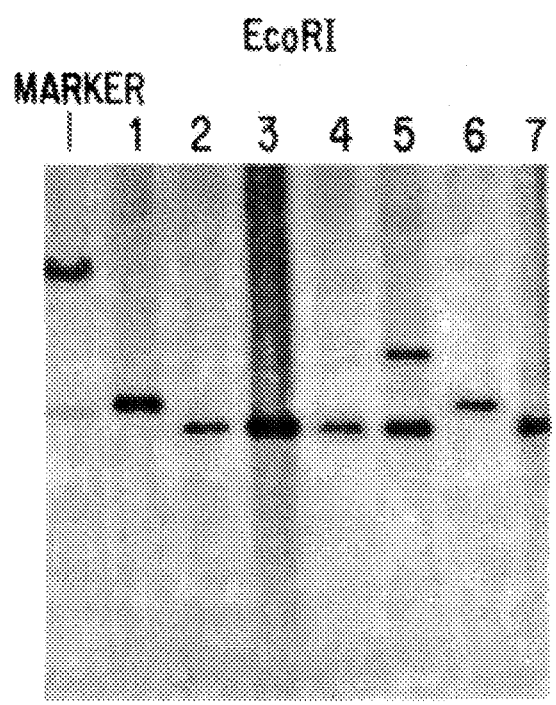
Figures 3A, 3B:
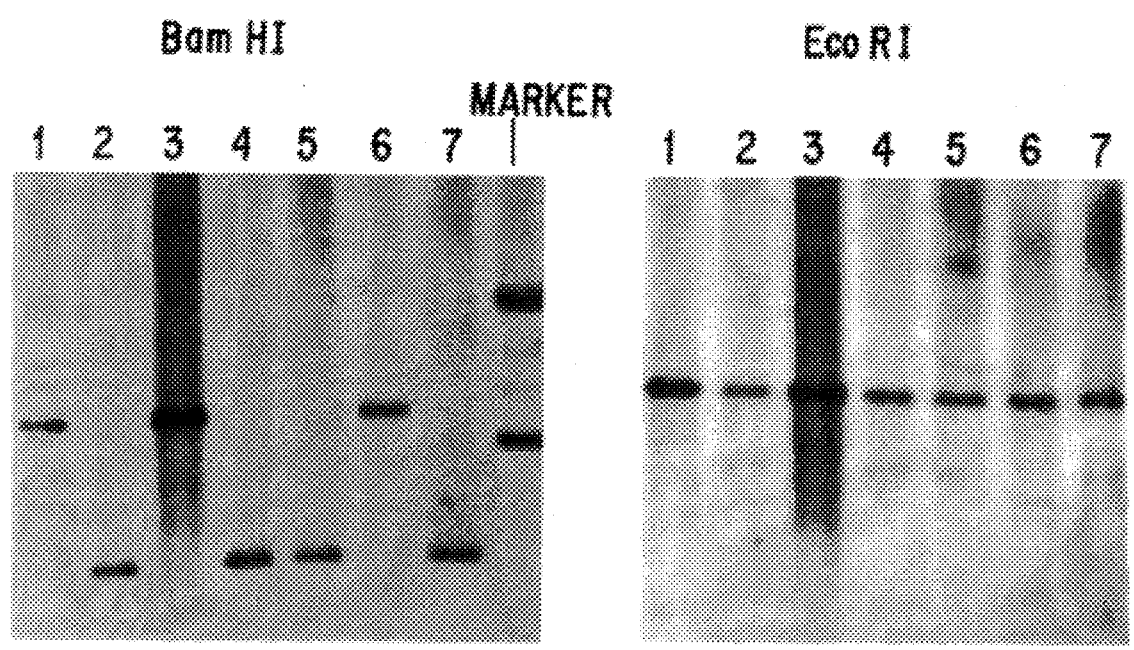
FIGS. 3A–3B are an electrophoretic pattern (2) showing the results of RFLP in mitochondorial DNAs of male sterile lines obtained by protoplast fusion (probe, atp 6). Lane: 1. Cabbage; 2. Cabbage, Radish, MS-1; 3. Cabbage, Radish, MS-2; 4. Japanese radish (Ogura CMS); 5. Hakuran MS-1; 6. Hakuran MS-2; 7. Hakuran MS-3.
Figure 4A:
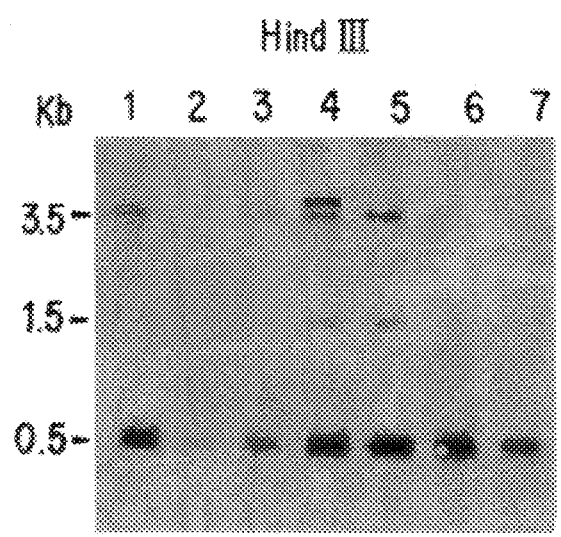
FIGS. 4A–4B are an electrophoretic pattern showing the results of RFLP in chloroplast DNAs of male sterile lines obtained by protoplast fusion (probe, EcoRI fragment of a chloroplast DNA). Lane: 1. Cabbage, Radish, MS-2; 2. Hakuran MS-1; 3. Hakuran MS-2; 4. Hakuran MS-3; 5. Cabbage; 6. Japanese radish (Ogura CMS); 7. Japanese radish (Normal).
Figure 4B:
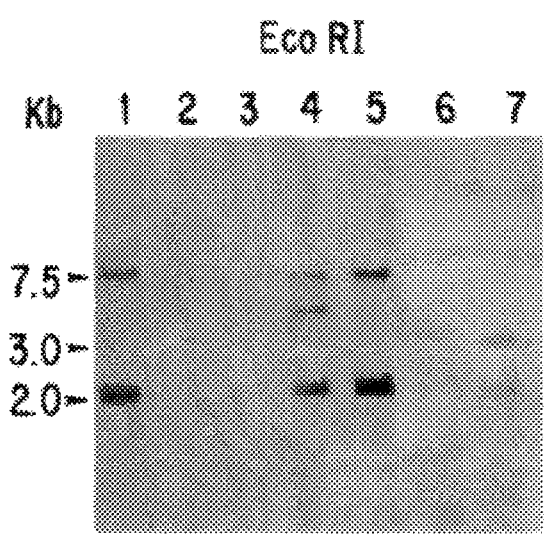
Figure 5A:
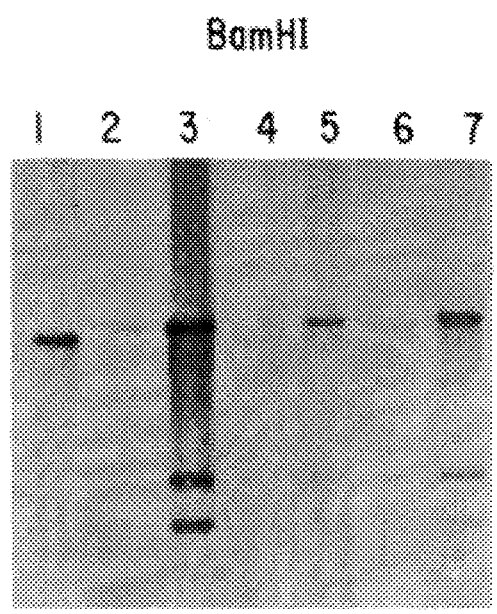
FIGS. 5A–5B are an electrophoretic pattern (3) showing the results of RFLP in mitochondorial DNAs of male sterile lines obtained by protoplast fusion [probe, cox I (+atp A)]. Lane 1. Cabbage; 2. Caggabe, Radish; MS-1, 3. Cabbage, Radish, MS-2; 4. Japanese radish (Ogura CMS); 5. Hakuran MS-1; 6. Hakuran MS-2; 7. Hakuran MS-3. Note: bands expressed in solid lines were obtained using coxI probes, while those expressed in dotted lines were obtained using atpA probes.
Figure 5B:
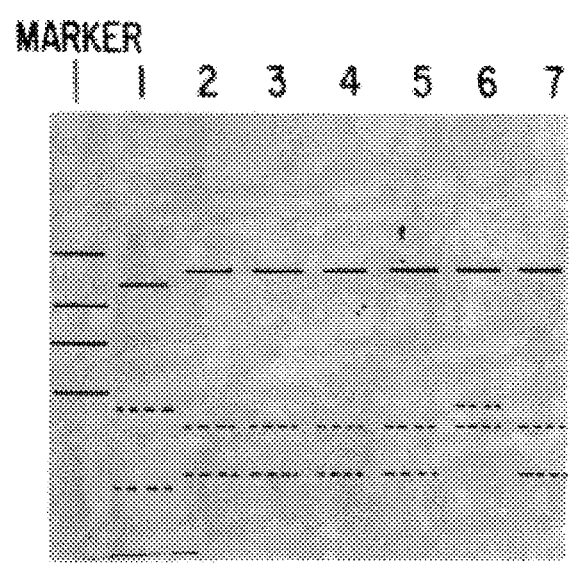
Figure 6A:
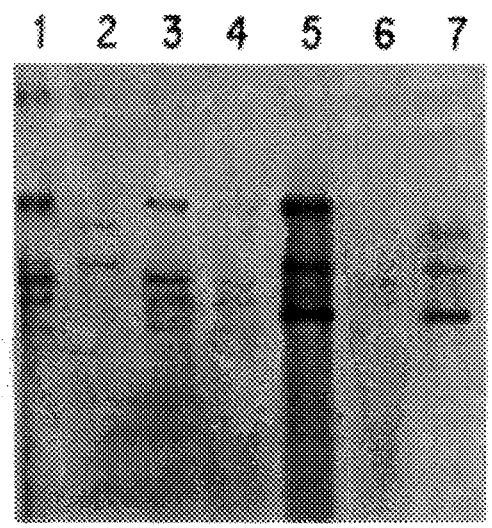
FIGS. 6A–6B are an electrophoretic pattern (4) showing the results of RFLP in mitochondorial DNAs of male sterile lines obtained by protoplast fusion [probe, cox I (+atp A)]. Lane: 1. Cabbage; 2. Cabbage, Radish, MS-1; 3. Cabbage, Radish, MS-2; 4. Japanese radish (Ogura CMS); 5. Hakuran MS-1; 6. Hakuran MS-2; 7. Hakuran MS-3. Note: bands expressed in solid lines were obtained using coxI probes, while those expressed in dotted lines were obtained using atpA probes.
Figure 6B:
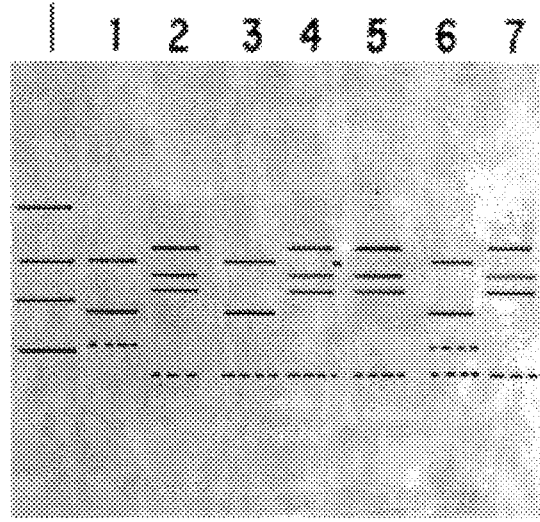
Figure 7:
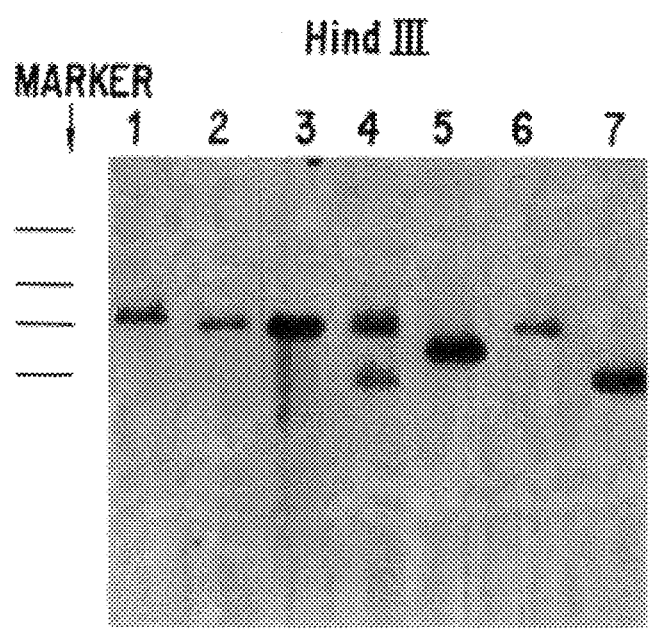
FIG. 7 is an electrophoretic pattern (5) showing the results of RFLP in mitochondrial DNAs of male sterile lines obtained by protoplast fusion (probe, atp A). Lane: 1. Cabbage; 2. Cabbage, Radish, MS-1; 3. Cabbage, Radish, MS-2; 4. Hakuran MS-1; 5. Hakuran MS-2; 6. Japanese radish (Ogura CMS); 7. Japanese radish (Normal).

With respect also to the chloroplast DNA, cpDNAs were extracted according to the aforementioned Kemble (1987) method similarly and then digested with HindIII and EcoRI. Thereafter, the Southern hybridization was carried out using cpDNA probes of the genus Brassica (FIGS. 2–7).

The results of this RFLP were given in Table 2.

TABLE 2

Results of RFLP Technique in mtDNAs and cpDNAs of male sterile plants

| Name of Line | atp A | | | atp 6 | | cox I | | cpDNA(a) | |
|---|---|---|---|---|---|---|---|---|---|
| | Bam | Eco | Hind | Bam | Eco | Bam | Eco | Eco | Hind |
| Cabbage . Radish . MS-1 | Og | Og | Og | Og | * | Og | Og | Cab | Cab |
| Cabbage . Radish . MS-2 | Og | Og | Og | Cab | * | Og | Cab | Cab | Cab |
| Hakuran MS-1 | Og | Rec | Rec | Og | * | Og | Og | Cab | Cab |
| Hakuran MS-2 | Rec | Cab | Rec | Cab | * | Og | Cab | Cab | Cab |
| Hakuran MS-3 | Og | Og | ND | Og | * | Og | Og | Rec | Rec |

In Table 2, "*" means that polymorphism could not be detected, "a" means a chloroplast probe, "Og" means being Ogura type, "Cab" means being cabbage type, "Rec" means being recombined type and "ND" means being unanalyzed.

As the result, with respect to Cabbage MS-1 (given as Cabbage•Radish•MS-1 in Table 2), it was found that its cpDNA was changed into that of cabbage type, as compared with the existing male sterile (Ogura) cytoplasm.

With respect to Cabbage MS-2 (given as Cabbage•Radish•MS-2 in Table 2), atp 6 and cox I in its mtDNA were changed into those of cabbage type and, in addition, its cpDNA was also changed into that of cabbage type.

With respect to Hakuran MS-1, it was found that a novel band was formed and that the recombination of genes attributable to protoplast fusion took place in atp A in its mtDNA.

With respect to Hakuran MS-2, a novel band attributable to recombination was formed in ATP-A in its mtDNA, similarly to the Hakuran MS-1.

With respect to Hakuran MS-3, no difference was recognized in mtDNA between said Hakuran MS-3 and the existing male sterile (Ogura) cytoplasm, similarly to the results of the aforementioned PCR technique. In the cpDNA, however, it became clear that a novel band was formed and thus the recombination took place.

As described in the above 1) and 2), it became clear that the combination of the PCR technique with the RFLP technique using a mtDNA and a cpDNA in a cytoplasm as indexes enables a determination of the difference of the concerned male sterile cytoplasm from the existing male sterile cytoplasm, and, simultaneously, enables classification and characterization of individual cytoplasms.

[Example 2]

Production of the desired male sterile plant according to back crossing

Among the somatic hybrid cell of the genus Brassica having novel male sterile cytoplasms obtained in Example 1, Cabbage MS-2 was supposed to be able to be hybridized with a group of conspecific crop varieties because its karyotype is the same as that of *Brassica oleracea*.

However, said plant had an increased chromosome number in comparison with the ordinary chromosome number of a plant of the species *oleracea* because of protoplast fusion.

Therefore, the ovule culture method was adopted jointly with the back crossing for the purpose of acquiring a progeny efficiently. That is, after said back crossing, 2-week-aged immature seeds were aseptically collected and then bred by placing the same on MS media with half the concentration containing 5% sucrose and 1 g/l Casamino acid, thereby obtaining progenies. By the joint adoption of said ovule culture method, Cabbage MS-2 was back crossed plural times with pure lines of a cabbage, a broccoli, a cauliflower, an ornamental kale, a kale, a kairan, a collard and a kohlrabi belonging to the species *oleracea* similarly to the Cabbage MS-2, thereby breeding a mother plant line of the genus Brassica carrying a highly pure nucleus of *Brassica oleracea* and a novel male sterile cytoplasm of Cabbage MS-2.

Incidentally, although said plant becomes closer to the pure line varieties subjected to the hybridization as the frequency of said back crossing increases, concrete judgement thereof was made according to the RAPD method [Williams, J. G. et al.; *Nucleic Acid Res.*, vol. 18, pp. 6531–6535 (1991)]. With respect to the nucleic DNA of the progeny obtained by said back crossing, the difference between the pure line variety and the hybridized variety was tested according to the RAPD method using a commercially available primer kit manufactured by Operon, Inc.(1,000 Atlantic Ave., Suite 108, Alameda, Calif., U.S.A.). As a result of this test, it was found that it was required to carry out back crossing about 7 times.

At this time, in order to test that the male sterility is preserved because a male sterile cytoplasm is transmitted only from the mother plant, a part of said plants having Cabbage MS-2 male sterile cytoplasms were isolated just before flowering to also confirm that seeds of self-fertilized progenies could not be obtained.

In the case of adopting a novel male sterile cytoplasm Hakuran MS-1 as a mother plant, synthetic rapeseeds having both nuclei of *Brassica oleracea* and *Brassica campestris* artificially produced according to the aforementioned ovule culture method and those of *Brassica campestris* were used for back crossing. In the case of adopting Hakuran MS-2 as a mother plant, a broccoli, a cauliflower and a cabbage belonging to *Brassica oleracea;* a Chinese cabbage, a turnip and zatsuna belonging to *Brassica campestris;* and a leaf mustard belonging to *Brassica juncea* were back crossed. In the case of adopting Hakuran MS-3 as a mother plant, a Chinese cabbage, zatsuna and kukidachina belonging to *Brassica campestris* were back crossed. In every case, the ovule culture method was jointly applied to the first generation or the first to the second generations to obtain progenies in said back crossing. With respect to the frequency of back crossing, the difference in nucleic DNA between each pure line variety used for said back crossing and each progeny obtained was tested according to the RAPD method, similarly to the case of the aforementioned Cabbage MS-2.

As the result, every case required carry out back crossing preferably about at least 7 times. In addition, with respect to male sterility in progenies, not only was it observed that pollen were not visually produced by it was also confirmed that seeds of self-fertilized progenies were not obtained when a part of the mother plants was isolated.

What is claimed is:

1. A male sterile Brassica plant comprising:

a plurality of cells each having a plurality of mitochondria and a plurality of chloroplasts;

mitochondrial DNA in each said mitochondrion exhibiting:

a first restriction fragment length polymorphism (RFLP) as analyzed with BamHI as a restriction enzyme and atpA as a probe which is identical to a corresponding identically analyzed RFLP of mitochondrial DNA contained in Ogura cytoplasm, a second RFLP as analyzed with EcoRI as a restriction enzyme and atpA as a probe which is identical to a corresponding identically analyzed RFLP of the Ogura mitochondrial DNA, a third RFLP as analyzed with HindIII as a restriction enzyme and atpA as a probe which is identical to a corresponding identically analyzed RFLP of the Ogura mitochondrial DNA, a fourth RFLP as analyzed with BamHI as a restriction enzyme and atpA as a probe which is identical to a corresponding identically analyzed RFLP of mitochondrial DNA contained in cabbage, a fifth RFLP as analyzed with BamHI as a restriction enzyme and coxI as a probe which is identical to a corresponding identically analyzed RFLP of the Ogura mitochondrial DNA, and a sixth RFLP as analyzed with EcoRI as a restriction enzyme and coxI as a probe which is identical to a corresponding identically analyzed RFLP of the cabbage mitochondrial DNA; and chloroplast DNA in each said chloroplast exhibiting:

a seventh RFLP as analyzed with EcoRI as a restriction enzyme and cpDNA(a) as a probe which is identical to a corresponding identically analyzed RFLP of chloroplast DNA contained in cabbage, and an eighth RFLP as analyzed with HindIII as a restriction enzyme and cpDNA(a) as a probe which is identical to a corresponding identically analyzed RFLP of cabbage chloroplast DNA.

2. A male sterile Brassica plant comprising:

a plurality of cells each having a plurality of mitochondria and a plurality of chloroplasts;

mitochondrial DNA in each said mitochondrion exhibiting:

a first restriction fragment length polymorphism (RFLP) as analyzed with BamHI as a restriction enzyme and atpA as a probe comprising a first large fragment (3.7 kbp) of a corresponding identically analyzed RFLP of mitochondrial DNA contained in Ogura cytoplasm and a second large fragment (4.1 kbp) of a corresponding identically analyzed RFLP of mitochondrial DNA contained in cabbage, a second RFLP as analyzed with EcoRI as a restriction enzyme and atpA as a probe which is identical to a corresponding identically analyzed RFLP of cabbage mitochondrial DNA, a third RFLP as analyzed with HindIII as a restriction enzyme and atpA as a probe comprising a third large fragment (6.6 kb) which is different from both a corresponding identically analyzed RFLP of the Ogura mitochondrial DNA and a corresponding identically analyzed RFLP of the cabbage mitochondrial DNA, a fourth RFLP as analyzed with BamHI as a restriction enzyme and atp6 as a probe which is identical to a corresponding identically analyzed RFLP of cabbage mitochondrial DNA, a fifth RFLP as analyzed with BamHI as a restriction enzyme and coxI as a probe which is identical to a corresponding identically analyzed RFLP of Ogura mitochondrial DNA, and a sixth RFLP as analyzed with EcoRI as a restriction enzyme and coxI as a probe which is identical to a corresponding identically analyzed RFLP of cabbage mitochondrial DNA; and chloroplast DNA in each said chloroplast exhibiting:

a seventh RFLP as analyzed with EcoRI as a restriction enzyme and cpDNA(a) as a probe which is identical to a corresponding identically analyzed RFLP of chloroplast DNA contained in cabbage, and an eighth RFLP as analyzed with HindIII as a restriction enzyme and cpDNA(a) as a probe which is identical to a corresponding identically analyzed RFLP of cabbage chloroplast DNA.

3. A male sterile Brassica plant comprising:

a plurality of cells each having a plurality of mitochondria and a plurality of chloroplasts;

mitochondrial DNA in each said mitochondrion exhibiting:

a first restriction fragment length polymorphism (RFLP) as analyzed with BamHI as a restriction enzyme and atpA as a probe which is identical to a corresponding identically analyzed RFLP of mitochondrial DNA contained in Ogura cytoplasm, a second RFLP as analyzed with EcoRI as a restriction enzyme and atpA as a probe which is identical to a corresponding identically analyzed RFLP of Ogura mitochondrial DNA, a third RFLP as analyzed with HindIII as a restriction enzyme and atpA as a probe which is identical to a corresponding identically analyzed RFLP of Ogura mitochondrial DNA, a fourth RFLP as analyzed with BamHI as a restriction enzyme and atp6 as a probe which is identical to a corresponding identically analyzed RFLP of Ogura mitochondrial DNA, a fifth RFLP as analyzed with BamHI as a restriction enzyme and coxI as a probe which is identical to a corresponding identically analyzed RFLP of Ogura mitochondrial DNA, and a sixth RFLP as analyzed with EcoRI as a restriction enzyme and coxI as a probe which is identical to a corresponding identically analyzed RFLP of Ogura mitochondrial DNA; and chloroplast DNA in each said chloroplast exhibiting:

a seventh RFLP as analyzed with EcoRI as a restriction enzyme and cpDNA(a) as a probe comprising a first large fragment (1.95 kbp) which is different from both a corresponding identically analyzed RFLP of chloroplast DNA contained in Ogura cytoplasm and a corresponding identically analyzed RFLP of chloroplast DNA contained in cabbage, and an eighth RFLP as analyzed with HindIII as a restriction enzyme and cpDNA(a) as a probe comprising a second large fragment (1.95 kbp) which is different from both a corresponding identically analyzed RFLP of Ogura chloroplast DNA and a corresponding identically analyzed RFLP of cabbage chloroplast DNA.

* * * * *

UNITED STATES PATENT AND TRADEMARK OFFICE
CERTIFICATE OF CORRECTION

PATENT NO. : 5,650,559
DATED : July 22, 1997
INVENTOR(S) : Toyokazu Akamatsu et al.

It is certified that error appears in the above-identified patent and that said Letters Patent is hereby corrected as shown below:

Column 3,
Line 26, "Note: $\gamma$-Hind III" should read -- Note: $\lambda$-Hind III --.

Column 4,
Line 44, "the ANANO" should read -- the ANAND --.

Column 8,
Line 49, "No. 4)." should read -- No. 6). --.

Column 13,
Line 65, "and atpA as" should read -- and atp6 as --.

Signed and Sealed this

Second Day of April, 2002

Attest:

JAMES E. ROGAN
*Director of the United States Patent and Trademark Office*

*Attesting Officer*

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

TGCGAGTCAA TCCACTAACT 20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

CTATTTGTTC CTTTACCAGG 20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

AACACTACTC TCATCCCTCG 20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

ATCTTTCGGC ACCTTGATCG 20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

AGCTTGGTAG CTCGCAAGGA 20

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

CTAGTTGAGG TCTGAAAGCC 20